United States Patent [19]

Roos

[11] 4,116,198
[45] Sep. 26, 1978

[54] ELECTRO - SURGICAL DEVICE

[75] Inventor: Eberhard Roos, Tuttlingen, Fed. Rep. of Germany

[73] Assignee: DELMA, elektro und medizinische Apparatebaugesellschaft m.b.H., Tuttlingen, Fed. Rep. of Germany

[21] Appl. No.: 686,600

[22] Filed: May 14, 1976

[30] Foreign Application Priority Data

May 15, 1975 [DE] Fed. Rep. of Germany ....... 2521719

[51] Int. Cl.² ............................................ A61B 17/32
[52] U.S. Cl. ............................................... 128/303.15
[58] Field of Search ....................... 128/303.13–303.18

[56] References Cited

U.S. PATENT DOCUMENTS

| 2,002,559 | 5/1935 | Wappler | 128/303.15 |
| 2,056,377 | 10/1936 | Wappler | 128/303.14 |
| 3,707,149 | 12/1972 | Hao et al. | 128/303.14 |
| 3,901,242 | 8/1975 | Storz | 128/303.15 |
| 3,920,021 | 11/1975 | Hiltebrandt | 128/303.17 |
| 3,987,795 | 10/1976 | Morrison | 128/303.14 |
| 3,990,456 | 11/1976 | Iglesias | 128/303.15 |
| 4,011,872 | 3/1977 | Komiya | 128/303.14 |

FOREIGN PATENT DOCUMENTS

| 1,209,247 | 2/1960 | France | 128/303.17 |
| 1,439,302 | 1/1969 | Fed. Rep. of Germany | 128/303.14 |
| 932,705 | 7/1963 | United Kingdom | 128/303.18 |

*Primary Examiner*—Lee S. Cohen

[57] ABSTRACT

Electro-surgical device with an insulated cable which can be passed through an endoscope, to which can be connected the pole of a high frequency generator, said pole being insulated from earth potential and on whose end facing the body cavity is provided a small-area treatment electrode projecting from the endoscope, said treatment electrode cooperating with a large-area neutral electrode connected to the other pole of the high frequency generator which is insulated from earth potential in such a way that due to the high current density in the area of the treatment electrode, a generation of heat takes place which is adequate for separating or coagulating tissue, wherein the large-area neutral electrode is arranged in the vicinity of the treatment electrode and is connected with the other pole of the high frequency generator by means of an insulated cable which can also be passed through the endoscope.

20 Claims, 9 Drawing Figures

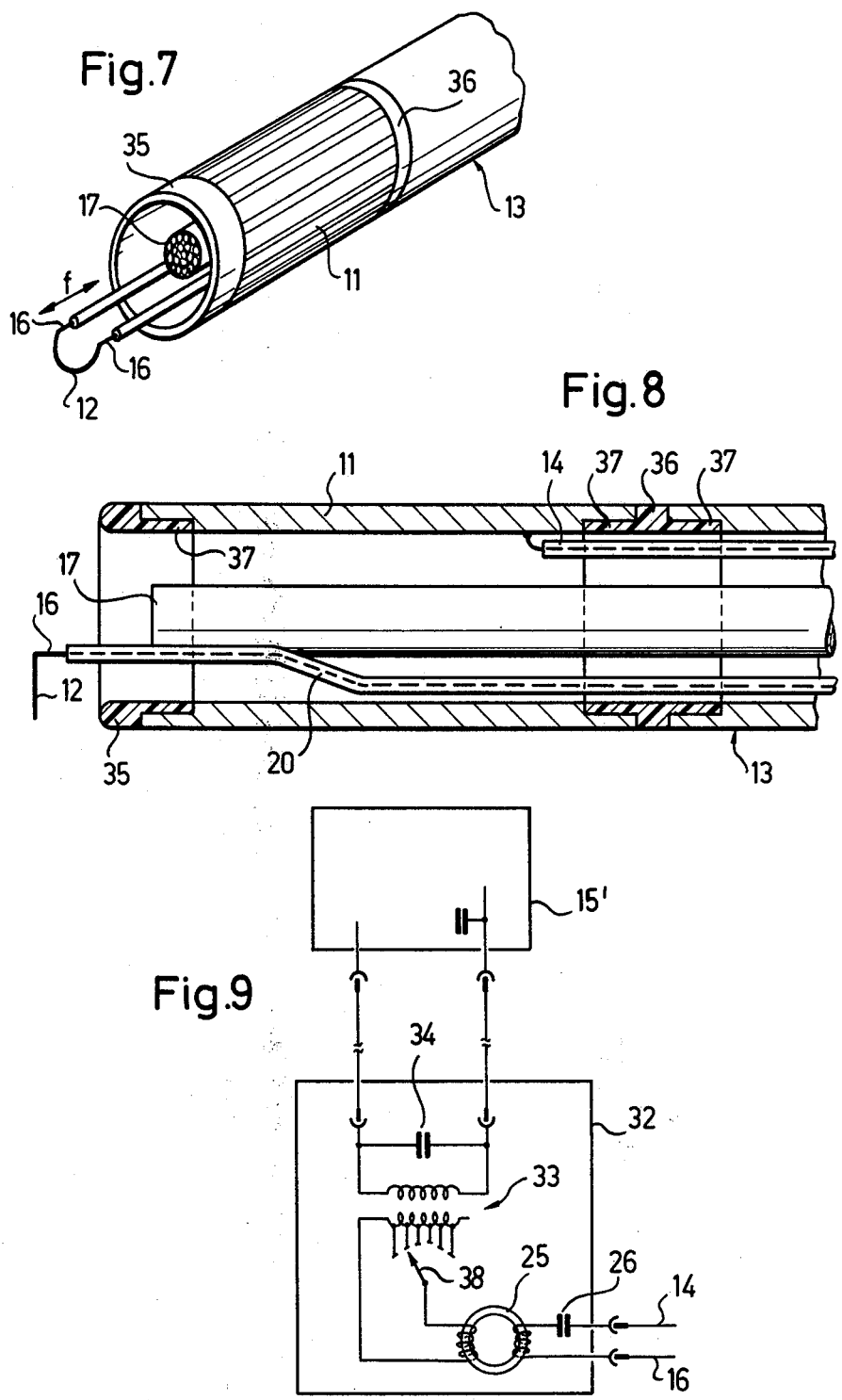

ELECTRO - SURGICAL DEVICE

BACKGROUND OF THE INVENTION

The invention relates to an electro-surgical device with an insulated cable which can be passed through an endoscope, to which can be connected the pole of a high frequency generator, said pole being insulated from earth potential and on whose end facing the body cavity is provided a small-area treatment electrode projecting from the endoscope, said treatment electrode cooperating with a large-area neutral electrode connected to the other pole of the high frequency generator which is insulated from earth potential in such a way that due to the high current density in the area of the treatment electrode, a generation of heat takes place which is adequate for separating or coagulating tissue.

Electro-surgical devices of this type permit electro-surgical operations of the filled bladder (electro-resection, e.g. of bladder tumors and the prostate glands) using endoscopes, particularly resectoscopes and cystoscopes.

The high degree of development in the endoscope field has resulted in operations in the bladder and on the prostate glands using these instruments and by means of electro-surgery have become the most commonly used operating procedure.

In known devices of this type, high frequency alternating current is fed via an earthed neutral electrode on the one hand and via a sparking ball or cutting loop well insulated relative to the outer shaft of the endoscope on the other to the operating area for coagulation purposes in the case of hemorrhages. Due to the relatively small area of the cutting loop compared to the area of the neutral electrode applied externally to the patient's body a very high current density occurs in the area of the cutting loop which results in heat generation in the tissue linked with the bursting of the tissue cells through steam generation and consequently a separation of the tissues. For the desired cutting or coagulating effects, the necessary power values of the high frequency current applied vary between 120 and 150 W.

As the leads from the high frequency generator to the cutting electrode have to be passed through the metallic endoscope, the distances between the high frequency-carrying lead and the remaining metal parts of the endoscope insulated therefrom are so small that capacitances of considerable size exist between these metal parts. Thus, to a certain extent, the endoscope forms a capacitor via which part of the applied capacity flows away as leakage current onto the tissue engaging with the metal endoscope shaft. A further, still larger portion of the applied capacity flows from the cutting loop via the washing water directly to the metal parts of the endoscope shaft located in the washing water flow and from there to the engaging tissue. Thus, uncontrollable electrical conditions in the urethral tissue engaging with the endoscope and the unequal distribution of lubricants with insulating properties on the endoscope shaft can cause critical current densities when the leakage current passes to the urethra and this results in burns.

These difficulties would not be eliminated by coating the endoscope shaft with tubes of high-grade insulating material, because the slightest damage to the shaft insulation due to the very high current densities occur during the passage of the leakage current would, in fact, increase the danger of burning due to the damage. However, if the endoscope shaft insulation remains intact, the entire leakage current is led off to the points where the operator is in contact with the endoscope leading to burns to the operator's face or to the eye in contact with the metal escutcheons of the transparent optics.

Neutral electrode isolation from earth potential cannot prevent the passage of the leakage currents to the operator. As the neutral electrode acts as an opposite pole to the cutting or coagulation electrode between the patient and the earthed operating table, it is capacitively connected to earth potential. Therefore, the cutting loop and the leakage current flown therefrom together with its voltage are earthed. Since, in any case, the operator largely carries the earth potential, the passage of the leakage current to the operator cannot be avoided by the measures in question.

BRIEF SUMMARY OF THE INVENTION

The problem of the invention is therefore to provide an electro-surgical device of the type indicated hereinbefore where undesired burns to the urethra and the operator are effectively avoided.

According to the invention, this problem is solved in that the large-area neutral electrode is arranged in the vicinity of the treatment electrode and is connected with the other pole of the high frequency generator by means of an insulated cable which can also be passed through the endoscope. In this way, potential compensation takes place in a spatially very narrowly defined zone. Both the treatment electrode, preferably constructed as a cutting loop and the neutral electrode carry no potential to earth. Leakage current does not flow to the endoscope shaft either from the high frequency lead to the treatment electrode or from the lead to the neutral electrode. Due to the existing capacitance, leakage currents only flow between the leads, but these do not have any external effects.

However, due to the small-area construction of the treatment electrode, a high current density is obtained there, which is adequate for tissue separation or coagulation, whereas the neutral electrode arranged in the immediate vicinity has such a large area that undesired heating is avoided there.

According to a preferred embodiment, the two feed leads comprise a coaxial cable, whose shield forms one conductor and is insulated relative to the endoscope. Thus, the two high frequency leads for the treatment and neutral electrode form a structural unit, which whilst taking up only a small amount of space, can be simply passed through the endoscope together with the optical and washing portions.

In general, the treatment electrode should be in loop form so that the operator's field of vision is uninterrupted.

According to a further embodiment, the centre conductor of the coaxial cable at the front projects above the shield and at this point passes into the treatment electrode. It is thereby particularly advantageous if the shield is constructed as a rigid sleeve and in such a way that the treatment electrode can be moved backwards and forwards relative to the endoscope via the coaxial cable. Thus, in this embodiment, the coaxial cable at the same time forms the support and operating member for the treatment electrode.

The relatively large neutral electrode is advantageously directly fixed to the coaxial cable shield. In this way the neutral electrode can be mounted reliably and immovably in an inexpensive and uncomplicated manner.

Advantageously, the neutral electrode is constructed as an elongated metal sheet slightly curved about the endoscope shaft and extending on either side over the coaxial cable.

According to a further advantageous embodiment, the endoscope has a plastic extension extending over a small portion only of its periphery, whereby the treatment electrode can be moved backwards and forwards beneath the said extension. This plastic extension has the advantage that the washing liquid can be satisfactorily guided and tissue which is not to be treated can be kept away from the treatment electrode. According to the invention, this extension can be used so that the large-area neutral electrode is fixed in insulated manner relative to the endoscope on the inside of the extension. The neutral electrode in then preferably connected with the high frequency generator by an insulated cable secured in the endoscope. In this case, only the other conductor with its insulation and treatment electrode is axially movable.

According to a particularly preferred embodiment, the coaxial cable has a bifurcation just before the body-side end of the endoscope and the two inner conductors eminating from the bifurcation are interconnected by a loop forming the treatment electrode. This construction is particularly stable due to the symmetry conditions resulting from the bifurcation, whereby at the same time the operator still has good visibility through the cutting loop forming the treatment electrode.

If the treatment electrode is used for coagulation purposes, a coagulation sparking ball is fitted to the treatment electrode.

The coaxial cable is advantageously surrounded by an insulating lead so as to prevent any connection of the endoscope metal with the high frequency voltage. Preferably, the insulating sleeve of the bifurcated coaxial cable is also bifurcated, but it extends only to just in front of the neutral electrode.

In the case of the bifurcated coaxial cable, the neutral electrode is preferably an elongated metal sheet, bent slightly around the endoscope shaft and extending from one branch of the bifurcation to the other. The sheet can have projections at the four corners which are placed around the shields. Depending on the degree of placing around and also clamping, any desired fixing of the neutral electrode to the coaxial cable can be obtained.

The current density in the area of the operating zone is advantageously influenced if the neutral electrode terminates at a distance from the end of the shield.

According to a further advantageous embodiment, the neutral electrode comprises two partial electrodes extending in the direction of the loop away from the two arms of the bifurcation. Preferably, the partial electrodes do not extend quite as far from the shields as the loop. At the front and rear ends the sheets preferably have rounded portions.

As a result of the slide-like construction, the operator can reliably guide the endoscope by placing the slide-like sheet projections on the tissue to then be removed. As is known, the endoscope is operated in such a way that the cutting loop is moved forwards relative to the endoscope, made live and then slowly retracted, whereby the tissue is removed by the heating on the cutting loop.

As stated hereinbefore, the treatment electrode and neutral electrode are appropriately so shaped and positioned that the illumination, vision and washing operations are not impaired by the endoscope.

Advantageously, the leads are inductively connected to the high frequency generator, whereby advantageously, a capacitor for filtering out low frequency voltage portions is preferably provided in one lead. This, in advantageous manner avoids faradic effects in the muscular system of the patient.

A capacitor is appropriately connected in parallel to the output winding of the transmitter which with the inductor of the latter forms an oscillating circuit which is tuned in such a way that the attenuation in the oscillating circuit formed by the leads, treatment electrode and neutral electrode is minimal.

BRIEF DESCRIPTION OF THE DRAWINGS

Other and further objects of the present invention will be apparent from the following description and claims and are illustrated in the accompanying drawings which, by way of illustration show preferred embodiments of the present invention and the principles thereof and what are now considered to be the best modes contemplated for applying these principles. Other embodiments of the invention embodying the same or equivalent principles may be used and structural changes may be made if desired by those skilled in the art without departing from the invention and the scope of the appended claims.

In the drawings show:

FIGS. 7 and 8 a perspective view and an axial section of a further advantageous embodiment.

FIG. 9 a schematic circuit diagram of an additional device for the device according to the invention.

DETAILED DESCRIPTION OF THE PREFERRED EMBODIMENTS

Figure 1:
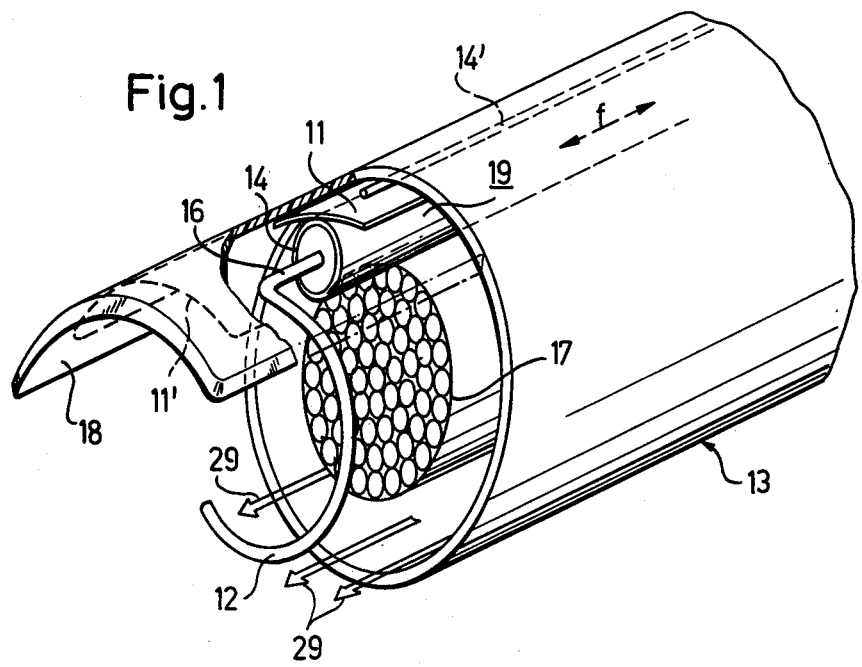
FIG. 1 a schematic, greatly enlarged perspective view of the front end of an endoscope equipped with the electro-surgical device according to the invention.

According to FIG. 1, an endoscope 13 is axial traversed in conventional manner by a fibre optical system 17, which is spaced relative to the sides of the endoscope 13, in such a way that washing liquid can pass through there (arrow 29) and there still remains space for the axial insertion of an electro-surgical treatment device.

According to the invention, this electro-surgical treatment device comprises a coaxial cable 19 with rigid metallic shield 14 and an inner conductor 16 axially inserted together with the fibre optical system 17. Inside the metallic shaft of the endoscope 13, the shield 14 is covered in not shown manner with an insulating sleeve 22, shown in the case of the constructions of FIGS. 2 and 3.

At the front, inner conductor 16 projects somewhat from the coaxial cable 19 and passes into the treatment electrode 12, which in general comprises a loop ensuring free visibility for the operator via the fibre optical systems 17.

The opposite electrode for the cutting electrode 12 is formed by a neutral electrode 11 fixed in electrically conductive manner to shield 14 and which is curved somewhat about the endoscope shaft, having a rectangular, elongated form shown in FIG. 1. Inner conductor 16 and shield 14 are connected, as shown in FIG. 4 to the two poles of a high frequency generator 15 which are not at earth potential.

At the front end of the metal shaft of the endoscope 13 is fixed a plastic extension 18, which is rounded and extends in the manner shown in FIG. 1, so as not to impair insertion, for example into the urethra. As the plastic extension 18 is an insulating body, the large-area neutral electrode 11' can also be fitted to the inside. It is then appropriately connected with the associated pole of the high frequency generator via a separate insulated conductor 14' in the endoscope, inside of via the shield 14.

Figure 4:
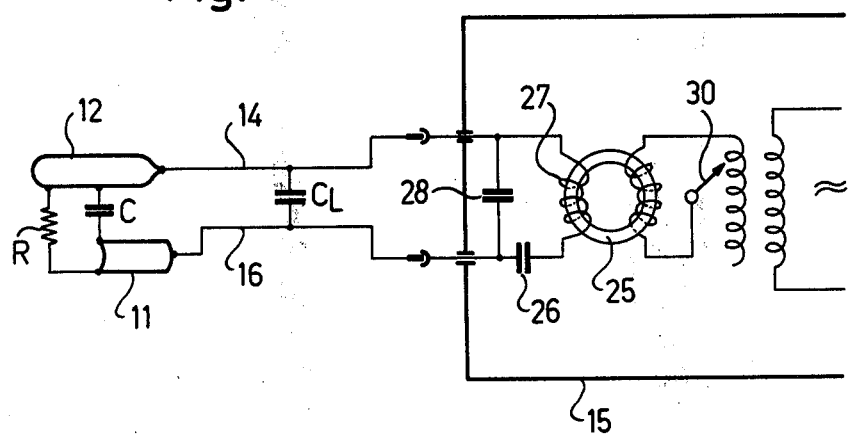
FIG. 4 a schematic circuit diagram of the electro-surgical device according to the invention with a particularly suitable high frequency generator.

As a result of the construction according to the invention, a high frequency field is only formed between shield 14 and inner conductor 16, as well as between neutral electrode 11 and treatment electrode 12, as is shown schematically in FIG. 4 by capacitors $C_L$ and C. Due to the current conduction through the tissue fluid and tissue itself, a true resistor R is also conceivable parallel to the capacitor between neutral electrode 11 and treatment electrode 12.

The supply to connect neutral electrode 11 and the treatment electrode 12 takes place by the inductive coupling of a high frequency voltage by means of a transformer 25, whose input voltage is regulatble by a variable tap 30. Due to the inductive coupling, the output lines 14 and 16 are galvanically isolated from earth potential.

A capacitor 26 connected in lead 16 is used for filtering out the low frequency current and therefore avoids faradic effects in the muscular system of the patient. A capacitor 28 connected in parallel to the output winding 27 of transformer 25 and behind capacitor 26 forms with the output winding an oscillating circuit tuned in such a way that the attenuation in the oscillating circuit formed from $C_L$, C and R as well as the inductors of lines 14, 16 is minimal.

As a result of the construction according to the invention, the leakage currents only flow between lines 14, 16 and therefore do not reach the metal shaft of endoscope 13. Thus, larger current densities such as are necessary for tissue separation or coagulation only occur outside the endoscope in the operating area.

Therefore, the danger of heating outside the desired area, as well as burns to the operator is reliably avoided.

Figure 2:
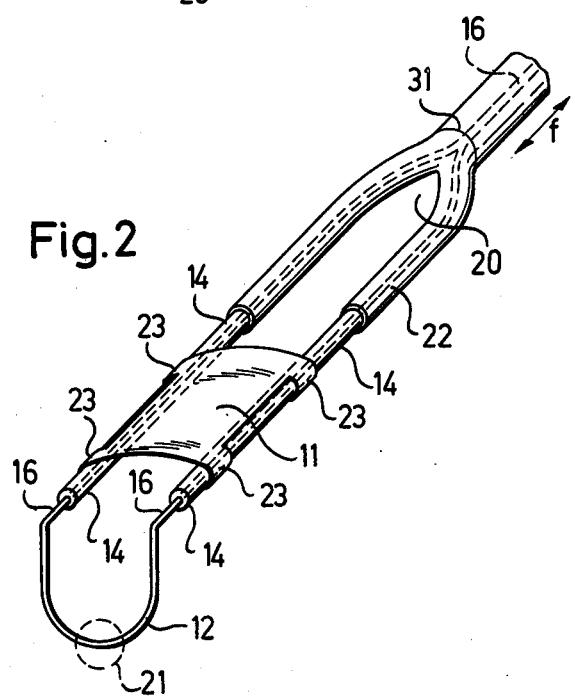
FIG. 2 a perspective view of a further embodiment of the electro-surgical device according to the invention, without the endoscope surrounding the same.

FIG. 2 shows a particularly advantageous embodiment of the electro-surgical device according to the invention in which both the inner conductor 16 and the shield 14 have a bifurcation 20. I$_n$ the same way, the insulating sleeve drawn over the shield 14 is bifurcated. The production of such a bifurcation is advantageously obtained by a welded joint at point 31 indicated by a line.

As a result of the bifurcation shown in FIG. 2, a cutting loop 12 can be arranged in the shown manner between the two inner conductors 16 eminating at the end. If the treatment electrode is to be used for coagulation, a coagulation sparking ball 21 can be provided on loop 12.

The construction of FIG. 2 is particularly well suited to the arrangement of a relatively large-area neutral electrode 11 which appropriately extends between the shields 14 of the two branches of the bifurcation 20, being slightly bent about the endoscope shaft. At the end, the neutral electrode 11 has projections 23 which are securely placed around the shields 14 for securing neutral electrodes 11 and for supplying the same with voltage. The metal sheeting forming the neutral electrode simultaneously constructionally reinforces the bifurcation 20, so that the guidance of the treatment electrode 12 by the operator is aided. As is known, the axial movement of the electro-surgical device in the direction of the double arrow f takes place by operating a pistol-like handle on endoscope 13, not shown in the drawing.

Figure 3:
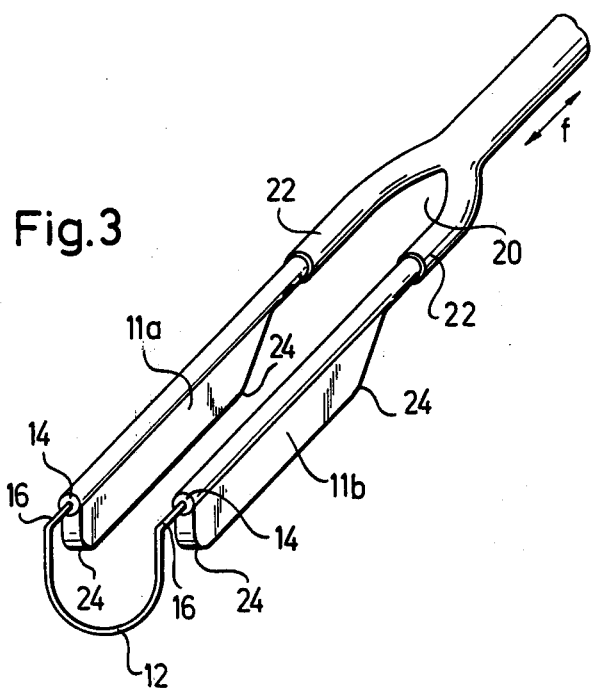
FIG. 3 a further embodiment of the electro-surgical device according to the invention, once again without a surrounding endoscope.

A further advantageous embodiment is shown in FIG. 3 where the neutral electrode is broken up into two partial electrodes 11a, 11b, which in the represented manner are soldered or welded to the shields 14 in such a way that the partial electrodes extend in the same direction as cutting loop 12. Rounded portions 24 are provided at both ends. The partial electrodes 11a, 11b applied to the shields 14 in this way thus additionally form slide-like support, by means of which the electro-surgical device can be placed on the tissue to be removed. This not only ensures a reliable guidance of the device but also ensures that the tissue is removed to the predetermined depth. The electrical advantages of limiting current conduction to the operating area are completely maintained.

Figure 5:
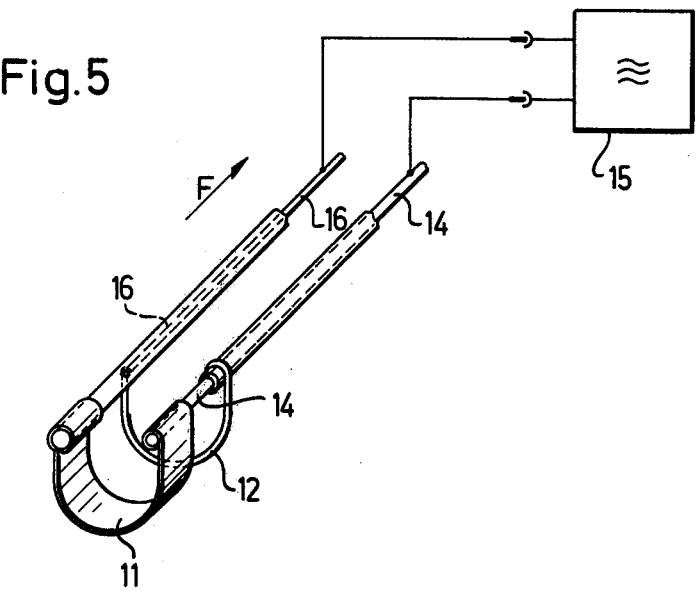
FIGS. 5 and 6 perspective views of two further advantageous embodiments

FIG. 5 shows a further advantageous embodiment, whereby only the front part of the electro-surgical device without the endoscope is shown. In this embodiment, two insulated cables with inner conductors 14, 16 are passed from high frequency generator 15 through the endoscope. At the front end are successively arranged the cutting loop 12 and the neutral electrode 11 constructed as a steel band. The cutting loop 12 is electrically conductively connected with the inner conductor 16, but at the other end is only fixed to the insulation surrounding the conductor 14. Conversely, the steel band 11, whose shape is similar to the cutting loop 12, is connected in electrically conductive and mechanically secure manner with the inner conductor 14, whilst the opposite end is mechanically secured to the insulation of the inner conductor 16. Since, according to the invention, the steel band 11 has the same radius as the wire loop, on retracting the loop 12 in the direction of arrow F, the band does not form an obstacle to the tissue portions removed by the loop. The neutral electrode 11 in the form of the steel band rests on the tissue in large-area form, so that good electrical contact is ensured.

Figure 6:
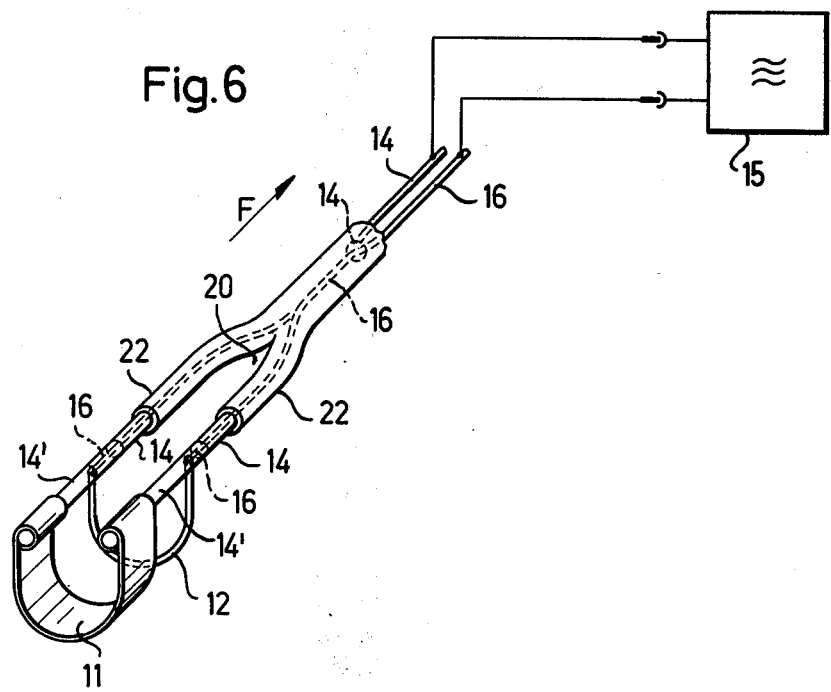

FIG. 6 shows an embodiment which is substantially the same as FIG. 5, whereby however, a bifurcated coaxial cable, similar to FIGS. 2 and 3 is used. The wire loop 12 is once again fixed to the inner conductors 16, whilst the neutral conductor 11 in band form is mechanically secured to extensions 14' electrically connected with the shield 14.

In the embodiment according to FIGS. 7 and 8, the front portion of endoscope 13 itself or a coaxial connection attached thereto at the front is constructed as the neutral electrode 11. To this end, the front portion is electrically insulated relative to the rear portion or the front-fitted connection from endoscope 13 by an intermediately inserted insulating ring 36. The cutting loop 12 can at the front be passed out of the neutral electrode 11 in one of the above-described manners. In the present embodiment, two leads 16 pass outwards from the cylindrical neutral electrode 11, which at 20 are combined to form a single cable, leading to the rear end of endoscope 13. The neutral electrode 11 is connected via a further insulated cable 14 to the high frequency generator 15 not shown in FIGS. 7 and 8.

It is also important in the case of the embodiments of FIGS. 7 and 8 that the cutting loop extends radially up to an insulating ring 35 mounted at the front on the neutral electrode 11 and can be retracted up to this. In this way, the front edge of the endoscope shaft, namely the front edge of the insulating ring 35 serves as a support for the cutting loop 12, so that the material is reliably removed therefrom. Therefore, as shown the insulating ring 35 must be rounded at the front.

Preferably, the insulating rings 35, 36 have axial attachments 37 with a reduced external diameter, by means of which a machanically secure fixing to the metal tubes is ensured.

FIG. 9 shows an additional device 32, by means of which a conventional high frequency surgical apparatus 15' with an earthed output terminal can be made usable for the purposes of the invention. The additional device 32 connected to the high frequency apparatus 15' has at the inlet a transformer 33 with parallel-connected capacitor 34 for tuning to the resonant frequency of the output circuit of the high frequency apparatus 15'. The output winding of transformer 33 is preferably regulatable by means of a loop arm 38 in such a way that the inductive output transformer 25 can receive voltages of varying sizes.

Via a capacitor 26, the output winding of transformer 25 is applied to the two output terminals of the additional device 32, where the leads 14, 16 can be applied.

In this way the high frequency apparatus 15' acquires an output with fluctuating potential, as is necessary for the connection of the electro-surgical device according to the invention.

The invention is not limited to the embodiments described and represented hereinbefore and various modifications can be made thereto without passing beyond the scope of the invention.

What is claimed is:

1. In combination: an endoscope having an endoscope body of substantially tubular shape, and an electro-surgical device comprising a treatment electrode projecting at one end from said endoscope body and a neutral electrode arranged adjacent said treatment electrode, insulated cable means for connecting said treatment electrode to one pole of a high-frequency generator, and means for connecting said neutral electrode to the other pole of a high-frequency generator, said endoscope body having an-insulating projection extending over a portion of the periphery of said endoscope body at said one end and having a front edge, said neutral electrode being located within said endoscope body and spaced a distinct distance inwardly from said front edge, a space being formed between said treatment electrode and said neutral electrode which is adapted to be filled with liquid to provide electrical conductance between said electrodes.

2. The combination of claim 1, wherein said insulated cable means and said means for connecting said neutral electrode to said other pole comprise coaxial cable means with shielding means forming one of said connecting means and being insulated relative to said endoscope body.

3. The combination according to claim 2, wherein said shielding means is constructed as a rigid sleeve in which said treatment electrode is adapted to be moved back and forth relative to said endoscope body through said coaxial cable means.

4. The combination according to claim 2, wherein said neutral electrode is fixed directly to said shielding means of said coaxial cable means.

5. The combination according to claim 4, wherein the neutral electrode is constructed as an elongated metal sheet slightly bent within said endoscope body and extending over said coaxial cable means.

6. The combination according to claim 2, comprising an insulating sleeve surrounding said coaxial cable means.

7. The combination according to claim 6, wherein said insulating sleeve is bifurcated and extends approximately to said neutral electrode.

8. The combination according to claim 7, wherein said neutral electrode is an elongated metal sheet slightly bent within said endoscope body and extending from one branch of said bifurcated insulating sleeve to the other.

9. The combination according to claim 8, wherein said sheet has projections at its four corners, two each of which are placed around the respective branches of said bifurcated sleeve.

10. The combination according to claim 2, wherein said neutral electrode terminates at a distance from said shielding means.

11. The combination according to claim 1, wherein said neutral electrode is secured to and insulated from said endoscope body on the inside of said insulating projection.

12. The combination according to claim 1, wherein said means for connecting said neutral electrode to said high-frequency generator is an insulated conductor secured in said endoscope body.

13. The combination according to claim 2, wherein said coaxial cable means has a bifurcation at that end of the endoscope body adjacent said projection, two inner conductors eminating from said bifurcation, and a loop interconnecting said two inner conductors and forming said treatment electrode.

14. The combination according to claim 1, wherein a coagulation sparking ball is fitted to said treatment electrode.

15. The combination according to claim 1, comprising a high-frequency generator, and wherein said cable means and said connecting means are inductively coupled to said high-frequency generator.

16. The combination according to claim 15, wherein a capacitor is connected in one of said cable means and said connecting means for filtering out low-frequency voltage.

17. The combination according to claim 15, wherein said generator comprises a transformer with an output winding having an inductor, a capacitor being connected parallel to said output winding and forming an oscillating circuit with said inductor, said circuit being tuned such that the attenuation in said circuit formed by said cable means, said connecting means, treatment electrode and neutral electrode is minimal.

18. The combination according to claim 15, comprising means for potential isolation connected between said high-frequency generator and said cable means and said connecting means respectively.

19. The combination according to claim 18, wherein said potential isolation means comprises a transformer, a capacitor connected parallel to said transformer, said high-frequency generator having an output circuit, said transformer and said output circuit being tuned in resonance.

20. The combination according to claim 19, comprising an inductive transformer connected to said transformer, said cable means and said connecting means being connected to said inductive transformer.

* * * * *